ized with a promoter selected from (i) aldehyde of formula $R^1CHO$

(12) United States Patent
Dennis-Smither et al.

(10) Patent No.: US 11,066,350 B2
(45) Date of Patent: Jul. 20, 2021

(54) PROCESS FOR DEHYDRATING METHANOL TO DIMETHYL ETHER

(71) Applicants: BP P.L.C., London (GB); BP (CHINA) HOLDINGS LTD, Shanghai (CN)

(72) Inventors: Benjamin James Dennis-Smither, Hull (GB); John Glenn Sunley, Hull (GB); Zhiqiang Yang, Liaoning (CN)

(73) Assignees: BP P.L.C., London (GB); BP (CHINA) HOLDINGS LTD, Shanghai (CN)

( * ) Notice: Subject to any disclaimer, the term of this patent is extended or adjusted under 35 U.S.C. 154(b) by 0 days.

(21) Appl. No.: 16/645,610

(22) PCT Filed: Aug. 23, 2018

(86) PCT No.: PCT/CN2018/101954
§ 371 (c)(1),
(2) Date: Mar. 9, 2020

(87) PCT Pub. No.: WO2019/037760
PCT Pub. Date: Feb. 28, 2019

(65) Prior Publication Data
US 2020/0262774 A1 Aug. 20, 2020

(30) Foreign Application Priority Data
Aug. 24, 2017 (WO) ................ PCT/CN2017/098892

(51) Int. Cl.
*C07C 41/09* (2006.01)

(52) U.S. Cl.
CPC .................................. *C07C 41/09* (2013.01)

(58) Field of Classification Search
None
See application file for complete search history.

(56) References Cited

U.S. PATENT DOCUMENTS

| 4,560,807 A | 12/1985 | Nobuyuki et al. |
| 2012/0220804 A1 | 8/2012 | Mitschke et al. |
| 2017/0081267 A1* | 3/2017 | Daniel .................... C07C 67/37 |
| 2017/0096382 A1 | 4/2017 | Beckers et al. |

FOREIGN PATENT DOCUMENTS

| CN | 1810752 | 8/2006 |
| CN | 1820849 | 8/2006 |
| CN | 101486629 | 7/2009 |
| CN | 104341279 | 2/2015 |
| CN | 105669452 | 6/2016 |
| EP | 1396483 | 10/2004 |
| WO | 199735823 A1 | 10/1997 |
| WO | 2004074228 | 9/2004 |
| WO | 2011027105 | 3/2011 |
| WO | 2013124404 | 8/2013 |
| WO | 2013124423 | 8/2013 |
| WO | 2014096254 | 6/2014 |
| WO | 2014125038 | 8/2014 |
| WO | 2015121411 | 8/2015 |
| WO | 2015193179 | 12/2015 |
| WO | 2015193182 | 12/2015 |
| WO | 2015193183 | 12/2015 |
| WO | 2015193185 | 12/2015 |
| WO | 2015193186 | 12/2015 |
| WO | 2015193188 | 12/2015 |

OTHER PUBLICATIONS

Foster, M.D., et al, Microporous and Mesoporous Materials, vol. 90, pp. 32-38, 2006.
The International Search Report with Written Opinion for PCT/CN2018/102072 dated Oct. 26, 20187, p. 1-11.
The International Search Report with Written Opinion for PCT/CN2017/098861 dated May 23, 2018, p. 1-11.
The International Search Report with Written Opinion for PCT/CN2018/102137 dated Nov. 28, 2018, p. 1-9.
The International Search Report with Written Opinion for PCT/CN2017/098885 dated May 30, 2018, p. 1-10.
The International Search Report with Written Opinion for PCT/CN2018/102057 dated Nov. 9, 2018, p. 1-11.
The International Search Report with Written Opinion for PCT/CN2017/098839 dated May 22, 2018, p. 1-11.
The International Search Report with Written Opinion for PCT/CN2018/101954 dated Nov. 19, 2018, p. 1-11.
The International Search Report with Written Opinion for PCT/CN2017/098892 dated May 22, 2018, p. 10.

* cited by examiner

*Primary Examiner* — Medhanit W Bahta
(74) *Attorney, Agent, or Firm* — McDonnell Boehnen Hulbert & Berghoff LLP

(57) ABSTRACT

A process for dehydrating methanol to dimethyl ether product in the presence of an aluminosilicate zeolite catalyst and a promoter selected from (i) aldehyde of formula $R^1CHO$ (Formula I) in which $R^1$ is hydrogen, a $C_1$-$C_{11}$ alkyl group or a $C_3$-$C_{11}$ alkyl group in which 3 or more carbon atoms are joined to form a ring; or (ii) acetal derivative of an aldehyde of Formula I; and the molar ratio of promoter to methanol is maintained at 0.1 or less.

21 Claims, 1 Drawing Sheet

PROCESS FOR DEHYDRATING METHANOL TO DIMETHYL ETHER

This application is a national stage application under 35 U.S.C. § 371 of International Application No. PCT/CN2018/101954, filed Aug. 24, 2018, which claims priority to International Application No. PCT/CN2017/098892, filed Aug. 24, 2017, the disclosures of which are explicitly incorporated by reference herein.

This invention relates in general to a dehydration process and in particular to a process for the dehydration of methanol in the presence of a zeolite catalyst and a promoter compound.

Industrial processes for the dehydration of methanol to dimethyl ether using catalysts such as alumina are known. Such processes employing alumina catalysts are described, for example in EP-A-1396483.

Processes for the dehydration of alcohols such as methanol employing dual catalyst systems incorporating zeolite catalysts are also known, for example in WO 2004/074228.

WO 2004/074228 describes a process for preparing dimethyl ether in high yield by employing a dual-catalyst system. Methanol is initially dehydrated over a hydrophilic solid acid catalyst such as gamma-alumina; unreacted methanol is then dehydrated over a second solid acid catalyst, a hydrophobic zeolite such as ZSM-5.

EP-A-1396483 and WO 2004/074228 exemplify the use of high reaction temperatures, typically 250° C. and higher. Whilst the use of such high reaction temperatures may be desirable to achieve acceptable reaction rates, a disadvantage is that at temperatures, typically in excess of 250° C., hydrocarbons are co-produced with the dimethyl ether product and this typically leads to a reduction in catalytic performance.

WO 2011/027105 describes a process for the simultaneous dehydration of methanol and hydrolysis of methyl acetate. The process can be conducted at reaction temperatures below 250° C. by employing a zeolite having a 2-dimensional framework structure comprising at least one channel having a 10-membered ring.

Processes for the co-production of acetic acid and dimethyl ether by the dehydration of methanol and hydrolysis of methyl acetate in the presence of zeolites having a 2-dimensional framework structure are also described, for example in WO 2013/124404 and WO 2013/124423.

Processes in which methanol-containing streams are dehydrated over various types of solid acid catalyst such as heteropolyacids, gamma-aluminas or zeolites are described, for example in WO 2015/193186 and WO 2015/193188.

Applicant has now found that compounds which are (i) aldehydes of Formula I $R^1CHO$ wherein $R^1$ is hydrogen, a $C_1$-$C_{11}$ alkyl group or a $C_3$-$C_{11}$ alkyl group in which 3 or more carbon atoms are joined to form a ring or (ii) acetal derivatives of aldehydes of Formula I have a beneficial effect on the rate of dehydration of methanol reactions carried out in the presence of aluminosilicate zeolites.

Accordingly, the present invention provides a process for dehydrating methanol to dimethyl ether product in the presence of a catalyst and a promoter, wherein the catalyst is at least one aluminosilicate zeolite and the promoter is at least one
  (i) aldehyde of formula $R^1CHO$ (Formula I)
    wherein $R^1$ is hydrogen, a $C_1$-$C_{11}$ alkyl group or a $C_3$-$C_{11}$ alkyl group in which 3 or more carbon atoms are joined to form a ring; or
  (ii) acetal derivative of an aldehyde of Formula I; and
wherein the molar ratio of promoter to methanol is maintained at 0.1 or less.

Advantageously, the promoters of the present invention allow productivity to dimethyl ether product to be improved in dehydration reactions of methanol which are carried out in the presence of aluminosilicate zeolites.

Also, according to the present invention there is provided a method of improving the productivity to dimethyl ether product in a process for dehydrating methanol in the presence of a catalyst and a promoter, wherein the catalyst is at least one aluminosilicate zeolite and the promoter is at least one
  (i) aldehyde of formula $R^1CHO$ (Formula I)
    wherein $R^1$ is hydrogen, a $C_1$-$C_{11}$ alkyl group or a $C_3$-$C_{11}$ alkyl group in which 3 or more carbon atoms are joined to form a ring; or
  (ii) acetal derivative of an aldehyde of Formula I; and
wherein the molar ratio of promoter to methanol is maintained at 0.1 or less.

Yet further according to the present invention there is provided the use of a promoter in a process for the catalytic dehydration of methanol to dimethyl ether to improve productivity to dimethyl ether product wherein the catalyst is at least one aluminosilicate zeolite and the promoter is at least one
  (i) aldehyde of formula $R^1CHO$ (Formula I)
    wherein $R^1$ is hydrogen, a $C_1$-$C_{11}$ alkyl group or a $C_3$-$C_{11}$ alkyl group in which 3 or more carbon atoms are joined to form a ring; or
  (ii) acetal derivative of an aldehyde of Formula I; and
wherein the molar ratio of promoter to methanol is maintained at 0.1 or less.

More advantageously, use of the promoters of the present invention in which $R^1$ is a $C_3$-$C_{11}$ branched alkyl chain group, such as a $C_3$-$C_7$ branched alkyl chain group, may also mitigate deactivation of a zeolite catalyst thereby improving stability of the zeolite catalyst.

A further aspect of the present invention provides a process for dehydrating methanol to dimethyl ether product in the presence of a catalyst, wherein the catalyst is at least one aluminosilicate zeolite, and wherein prior to using the catalyst in the dehydration process, the catalyst has been impregnated with a promoter, wherein the promoter is at least one
  (i) aldehyde of formula R1CHO (Formula I)
    wherein R1 is hydrogen, a C1-C7 C11 alkyl group or a C3-C7 C11 alkyl group in which 3 or more carbon atoms are joined to form a ring; or
  (ii) acetal derivative of an aldehyde of Formula I.

Figure 1:
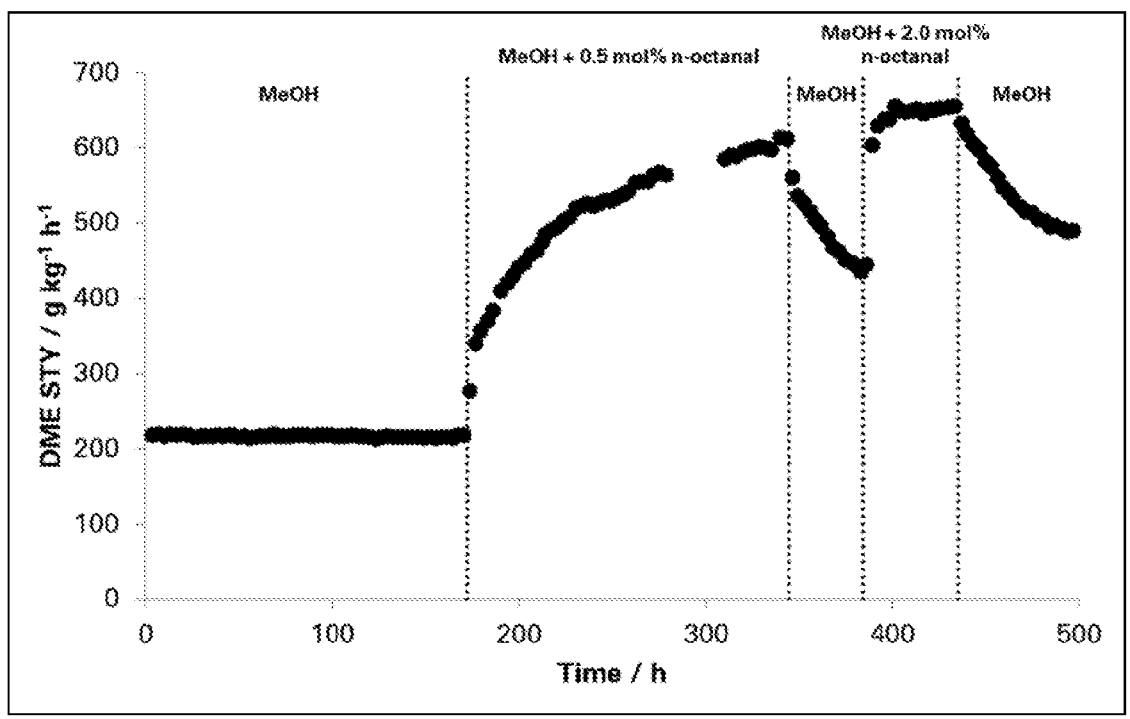
FIG. 1 depicts STY (space time yield) to dimethyl ether at varying concentrations of n-octanal promoter in the dehydration of methanol using the zeolite H-ZSM-22 as catalyst.

The catalytic dehydration reaction of methanol can be represented by the following equation: 2 methanol⇌dimethyl ether+water.

In the present invention, the dehydration process is carried out in the presence of at least one aluminosilicate zeolite as catalyst.

Aluminosilicate zeolites are crystalline microporous materials which have framework structures constructed from tetrahedra of $SiO_4$ and $AlO_4$ that share vertices. Such tetrahedral species are generally referred to as $TO_4$ species wherein the T atom is silicon or aluminium. Aluminium 'T' atoms can be partially or wholly replaced by one or more gallium, boron or iron atoms. For the purposes of the present invention, such gallium, boron or iron modified zeolites are considered to fall within the definition of the term 'aluminosilicate zeolites'.

Silicoaluminophosphate structures containing $PO_4$ tetrahedra are not considered to be aluminosilicate materials and consequently, such silicoaluminophosphates, for example SAPO-type materials, are not within the scope of the present invention.

A zeolite framework topology contains a regular array of pores, channels and/or pockets that vary in size, shape and dimensionality. These framework topologies or structure types of zeolites are assigned three-letter structure codes by the Structure Commission of the International Zeolite Association, under the authority of IUPAC.

A description of zeolites, their framework codes, structure, dimensionality, properties and methods of synthesis can be found in The *Atlas of Zeolite Framework Types* (C. Baerlocher, W. M. Meier, D. H. Olson, 5*th* Ed. Elsevier, Amsterdam, 2001) in conjunction with the web-based version (http://www.iza-structure.org/databases/).

Zeolite crystals contain pore or channel systems of molecular dimensions with fixed geometry and size and can be classified according to the number of channels running in different directions within the zeolite framework structure. A zeolite is described as 1-dimensional, 2-dimensional or 3-dimensional if the zeolite has one, two or three channels in different directions, respectively. Zeolites for use in the present invention may possess a 1-dimensional, a 2-dimensional or a 3-dimensional framework structure.

In some or all embodiments of the present invention the zeolite has a 1-dimensional framework structure. Specific non-limiting examples of such zeolites include zeolites selected from framework types MOR, MTT or TON. Examples of zeolites having framework type MOR include mordenite. Examples of zeolites having framework type MTT include ZSM-23. Examples of zeolites having framework type TON include ZSM-22 and theta-1.

In some or all embodiments of the present invention the zeolite has a 2-dimensional framework structure. Specific non-limiting examples of such zeolites include zeolites selected from framework types MWW or FER. Examples of zeolites having framework type MWW include PSH-3 and MCM-22. Examples of zeolites having framework type FER include ferrierite and ZSM-35.

In some or all embodiments of the present invention the zeolite has a 3-dimensional framework structure. Specific non-limiting examples of such zeolites include zeolites selected from framework types MFI, FAU, CHA and BEA. Examples of zeolites of framework type MFI include ZSM-5. Examples of zeolites of framework type FAU include zeolite Y and zeolite X. Examples of zeolites of framework type CHA include chabazite, SSZ-13 and SSZ-62. Examples of zeolites of framework type BEA include zeolite beta and SSZ-26.

Zeolites may also be classified according to the size of their pores. Zeolites with pore openings limited by 8 T atoms in tetrahedral co-ordination are defined as "small pore zeolites" (8-membered rings). Zeolites with pore openings limited by 10 T atoms in tetrahedral co-ordination are defined as "medium pore zeolites" (10-membered rings). Zeolites with pore openings limited by 12 T atoms in tetrahedral co-ordination are defined as "large pore zeolites" (12-membered rings).

For use in the present invention, the zeolite may be a small, medium or large pore zeolite. However, preference is given to large pore zeolites.

In some or all embodiments of the present invention, the zeolite is a small pore zeolite. Specific non-limiting examples of small pore zeolites include those of framework type CHA.

In some or all embodiments of the present invention, the zeolite is a medium pore zeolite. Specific non-limiting examples of medium pore zeolites include those of the framework types FER, MFI, MWW, MTT and TON and also ITQ-type zeolites, such as ITQ-13 and ITQ-34

In some or all embodiments of the present invention, the zeolite is a large pore zeolite.

Specific non-limiting examples of large pore zeolites include those of framework types, MOR, FAU, BEA, GME, IWW, MAZ, LTL and OFF and ITQ-type zeolites such as ITQ-7 and ITQ-26.

In some or all embodiments of the present invention, the zeolite is selected from zeolites of framework type FER, MWW, MTT, MFI, MOR, FAU, CHA, BEA and TON. Specific non-limiting examples of zeolites belonging to these framework types are ferrierite, ZSM-35, PSH-3, MCM-22, ZSM-23, ZSM-5, mordenite, zeolite Y, SSZ-13, zeolite beta and ZSM-22.

Typically, zeolites are synthesised from synthesis mixtures comprising a silica source, an alumina source, alkali metal hydroxide and water in desired proportions. The synthesis mixture is maintained, with or without agitation, under temperature, pressure and time conditions sufficient to form a crystalline aluminosilicate zeolite. The resulting zeolite contains alkali metal as a cation. Such cations may be replaced by known ion-exchange techniques. For example, the zeolite may be contacted with aqueous solutions of ammonium salts to substitute ammonium ions for the alkali metal cations. Ammonium-form zeolites are also available commercially.

Whilst zeolites in their ammonium-form can be catalytically active, for use in the present invention it is preferred to utilise a zeolite in its hydrogen-form (H-form). H-form zeolites are commercially available. Alternatively, an ammonium-form zeolite can be converted to the H-form by known techniques, for example by calcination under air or an inert gas at high temperature, for example at a temperature of 500° C. or higher.

In some or all embodiments of the present invention, a zeolite is a hydrogen-form (H-form) zeolite.

For use in the present invention, a zeolite may be composited with at least one binder material. The binder material may be a refactory inorganic oxide, such as silicas, aluminas, alumina-silicates, magnesium silicates, magnesium aluminium silicates, titanias and zirconias.

For use in the present invention, the relative proportions of zeolite and binder material in the composite may vary widely. Suitably, the binder material can be present in an amount of from 10% to 90% by weight of the composite.

For use in the present invention, the silica to alumina molar ratio of the zeolite may vary widely but suitably is in the range 10 to 300, for example in the range 20 to 280, such as in the range 20 to 100.

Promoter compounds for use in the present invention are selected from (i) aldehydes of Formula I $R^1CHO$, wherein $R^1$ is hydrogen, a $C_1$-$C_{11}$ alkyl group or a $C_3$-$C_{11}$ alkyl group in which 3 or more carbon atoms are joined to form a ring or (ii) acetal derivatives of the aldehydes of Formula I. Mixtures of aldehydes of Formula I and their acetal derivatives may also be used in the present invention.

In some or all embodiments of the present invention, $R^1$ is hydrogen, a $C_1$-$C_7$ alkyl group or a $C_3$-$C_7$ alkyl group in which 3 or more carbon atoms are joined to form a ring.

In some or all embodiments of the present invention, $R^1$ is a $C_3$-$C_{11}$ alkyl group, such as a $C_3$-$C_7$ alkyl group, for example n-butyl, isobutyl, tert-butyl, n-pentyl, n-hexyl, n-heptyl or n-octyl alkyl group.

In the present invention, $R^1$ may be a straight chain $C_1$-$C_{11}$ alkyl group or a branched chain $C_3$-$C_{11}$ alkyl group.

In some or all embodiments of the present invention, $R^1$ is a straight chain alkyl group and the aldehyde of Formula I is selected from n-butanal, n-hexanal and n-octanal.

Advantageously, Applicant has found that the use of aldehydes of Formula I in which $R^1$ is a $C_3$-$C_{11}$ branched chain alkyl group in zeolite-catalysed methanol dehydration reactions can lead to improved stability of the catalyst compared to the use of the corresponding $C_3$-$C_{11}$ straight chain aldehyde.

Thus, further according to the present invention, there is provided the use of an aldehyde compound to improve productivity to dimethyl ether product and reduce catalyst deactivation in a process for the catalytic dehydration of methanol to dimethyl ether product wherein the catalyst is at least one aluminosilicate catalyst and the aldehyde compound is at least one aldehyde of formula $R^1CHO$ wherein $R^1$ is a branched chain $C_3$-$C_{11}$ alkyl group, such as a branched chain $C_3$-$C_7$ alkyl group.

There is also provided a method of improving the productivity to dimethyl ether product and stability of a catalyst in a process for the catalytic dehydration of methanol to dimethyl ether product in the presence of a zeolite catalyst and an aldehyde compound wherein the catalyst is at least one aluminosilicate catalyst and the promoter is at least one aldehyde of formula $R^1CHO$ wherein $R^1$ is a branched chain $C_3$-$C_{11}$ alkyl group, such as a branched chain $C_3$-$C_7$ alkyl group.

In some or all embodiments of the present invention, $R^1$ is a branched chain $C_3$-$C_7$ alkyl group and suitably the aldehyde of Formula I is selected from iso-butanal and 2-ethyl hexanal.

In some or all embodiments of the present invention, in the aldehyde of Formula I, $R^1$ is a $C_3$-$C_7$ alkyl group in which 3 or more carbon atoms are joined to form a ring. Suitably, 4 to 7 carbon atoms may be joined to form a ring, such as 4 to 6 carbon atoms. Non-limiting examples of such aldehyde compounds are cyclopentanecarboxaldehyde, cyclohexanecarboxaldehyde and cycloheptanecarboxaldehyde.

The extent to which the dehydration reaction is promoted may vary depending on factors such as the structure of the zeolite and nature of the aldehyde or acetal promoter employed in the reaction. Usefully there is employed in the dehydration process a zeolite which is a large pore zeolite and an aldehyde of Formula I in which $R^1$ is a straight or branched chain $C_3$-$C_{11}$ alkyl group, such as a branched chain $C_3$-$C_7$ alkyl group, or a medium pore zeolite and an aldehyde of Formula I in which $R^1$ is a straight chain $C_3$-$C_{11}$ alkyl group, such as a straight chain $C_3$-$C_7$ alkyl group, or a 2-dimensional medium pore zeolite and an aldehyde of Formula I in which $R^1$ is a branched chain $C_3$ alkyl group.

Thus, in some or all embodiments of the present invention, there is employed in the dehydration process a zeolite which is a large pore zeolite of framework type selected from MFI, MOR, BEA and FAU, for example ZSM-5, mordenite, zeolite beta and zeolite Y respectively and an aldehyde of Formula I in which $R^1$ is a straight or branched chain $C_3$-$C_{11}$ alkyl group, such as a branched chain $C_3$-$C_7$ alkyl group.

In some or all embodiments of the present invention, there is employed in the dehydration process a zeolite which is a medium pore zeolite of framework type selected from FER, MWW, TON and MTT, for example ferrierite, PSH-3, MCM-22, ZSM-22 and ZSM-23 and an aldehyde of Formula I in which $R^1$ is a straight chain $C_3$-$C_1$ alkyl group, such as a straight chain $C_3$-$C_7$ alkyl group.

In some or all embodiments of the present invention, in the aldehyde of Formula I, $R^1$ is a branched chain $C_3$-$C_7$ alkyl group and suitably the aldehyde is iso-butanal and suitably the zeolite catalyst is of framework type FER, for example ferrierite or ZSM-35.

In some or all embodiments of the present invention, there is employed in the dehydration process an aldehyde of Formula I in which $R^1$ is a branched chain $C_3$ alkyl group and a zeolite which is a 2-dimensional medium pore zeolite, suitably of a framework type selected from FER or MWW, for example ferrierite, ZSM-35, PSH-3 and MCM-22.

Acetal derivatives of the aldehydes of Formula I also function as promoters in the present invention. In the present invention, the term 'acetal derivative' also includes the hemi-acetal derivatives of the aldehydes of Formula I. As would be readily understood by a person skilled in the art, an acetal is a functional group derived from an aldehyde by replacement of the carbonyl group of the aldehyde by two alkoxy groups. A hemi-acetal is derived from an aldehyde by replacement of the carbonyl group of the aldehyde by an alkoxy group and a hydroxyl group. Consequently, the acetal derivatives of the aldehydes of Formula I may be represented by the general structural formula:

(Formula II)

wherein $R^1$ has the meaning ascribed above in Formula I and each of $R^2$ and $R^3$ is an alkyl group or hydrogen with the proviso that $R^2$ and $R^3$ are not both hydrogen.

Suitably, each of $R^2$ and $R^3$ is an alkyl group which alkyl group is a $C_1$ to $C_6$ straight or branched chain alkyl group. In these instances, $R^2$ and $R^3$ may be identical or different.

In some or all embodiments of the present invention, $R^2$ and $R^3$ are each selected from a $C_1$ or $C_2$ alkyl group. In these embodiments $R^2$ and $R^3$ may be identical or different.

In some or all embodiments of the present invention, $R^2$ and $R^3$ are identical and each is a $C_1$ alkyl group. In this instance, the acetal derivative of Formula II is a dimethoxyacetal. Specific non-limiting examples of dimethoxy acetals are dimethoxymethane, 1,1-dimethoxyethane and 1,1-dimethoxyheptane.

In some or all embodiments of the present invention, the acetal derivative of the aldehyde of Formula I is a hemi-acetal. Suitably, in these embodiments one of $R^2$ and $R^3$ is hydrogen and one of $R^2$ and $R^3$ is a $C_1$ to $C_6$ alkyl group, for example a $C_1$ to $C_3$ alkyl group. Suitably, the hemi-acetal is a methoxy hemi-acetal.

In some or all embodiments of the present invention, the aldehyde of Formula I is a cyclic aldehyde which cyclic aldehyde has 4 to 8 carbon atoms, for example 4 to 6 carbon atoms. Suitably, in these embodiments $R^2$ and $R^3$ of the acetal derivative of the cyclic aldehyde are each a $C_1$ to $C_2$ alkyl group and may be identical or different. Suitably, in these embodiments, $R^2$ and $R^3$ are identical and may be a $C_1$ alkyl group.

In some or all embodiments of the present invention, the acetal derivative is a dimethoxyacetal, for example dimethoxymethane and 1,1-dimethoxyethane and the zeolite is a zeolite of framework type selected from TON, MOR and FER, for example ZSM-22, mordenite and ferrierite respectively.

Aldehydes of Formula I and their acetal derivatives are available commercially.

In the present invention, a promoter may be added as a component of the feed to the dehydration process. Alternatively and/or additionally, a promoter may be generated in-situ by the addition to the process of any compound (a precursor compound) from which an aldehyde of Formula I or an acetal derivative thereof can be generated in-situ.

Suitable precursor compounds for the aldehyde compounds of Formula I include the acetal derivatives thereof.

The aldehyde compounds of Formula I may also be generated in-situ via retro aldol-type condensation reactions of β-hydroxyaldehyde compounds or a compound resulting from loss of water therefrom. For example, where it is desired to generate the promoter compound, acetaldehyde in-situ in the dehydration process, a suitable precursor compound which may added to the process may be butenal or the β-hydroxyaldehyde, 3-hydroxybutanal.

In some or all embodiments of the present invention, a promoter precursor compound is a β-hydroxyaldehyde compound or a compound resulting from loss of water therefrom.

In the present invention the molar ratio of promoter to methanol is maintained at 0.1 or less. In some or all embodiments of the present invention the molar ratio of promoter to methanol is maintained in the range 0.00001:1 to 0.1:1. Non-limiting examples of suitable molar ratio ranges of promoter to methanol include 0.00002 to 0.1:1, 0.00005 to 0.1:1, 0.0001 to 0.1:1, 0.0005 to 0.1:1, 0.001:1 to 0.1:1, 0.001:1 to 0.05:1, and 0.002:1 to 0.05:1.

In the present invention the total amount of promoter relative to the total amount of methanol is maintained in an amount of at least 1 ppm and suitably up to 10 mol %. In some or all embodiments of the present invention, the total amount of promoter relative to the total amount of methanol is maintained throughout the dehydration reaction in an amount of at least 0.0005 mol %, for example in an amount of 0.0005 mol % up to 10 mol %, such as 0.0005 mol % to 5 mol %, for instance 0.001 mol % to 5 mol %. In some or all embodiments of the present invention, the total amount of promoter relative to the total amount of methanol is maintained throughout the dehydration reaction in an amount of at least 0.01 mol %, for example in an amount of 0.01 mol % to less than 10 mol %, such as 0.01 mol % to 5 mol %, for instance 0.05 to 5 mol %. In some or all embodiments of the present invention, the total amount of promoter relative to the total amount of methanol is maintained throughout the dehydration reaction in an amount of at least 0.1 mol % and suitably up to 10 mol %, for example in an amount of 0.1 to 5 mol %, such as 0.2 mol % to 5 mol %.

In some or all embodiments of the present invention, the catalyst may be impregnated with the promoter prior to being used in the dehydration process. The method of impregnation is not limited and any technique known in the art may be used, for example, incipient wetness technique or excess solution technique. The incipient wetness technique is so-called because it requires that the volume of impregnating solution be predetermined so as to provide the minimum volume of solution necessary to just wet the entire surface of the support, with no excess liquid. The excess solution technique as the name implies, requires an excess of the impregnating solution, the solvent being thereafter removed, usually by evaporation. The promoter may be used as the impregnation solution directly, or a dilute solution of the promoter may be used. When a dilute solution of promoter is used, the solvent for the impregnation solution may suitably be an aqueous solution, an organic solution, or a mixture of aqueous and organic solvent(s), depending upon the solubility of the promoter being used; non-limiting examples of suitable solvents include water, alcohols, for example methanol, ethers, and mixtures thereof, such as aqueous alcoholic solutions, for example an aqueous methanol solution.

Suitably, in the present invention, the dehydration process may be carried out as a standalone process. In such cases the dehydration reaction is not, for example carried out as part of a co-production process, such as co-production processes for the production of acetic acid and dimethyl ether by dehydration of methanol and hydrolysis of a methyl acetate co-feed. Thus, suitably, in the present invention, the feed components to the process are methanol and at least one compound selected from promoter and promoter precursor compounds.

However, typically, the product stream of the methanol dehydration reaction will comprise dimethyl ether, water, unconverted methanol and one or more compounds selected from promoter compounds and promoter precursor compounds. Thus, in some or all embodiments of the present invention, one or more components of the product stream of the dehydration process are recycled as feed to the process. In such instances one or both of dimethyl ether and water are additional feed components to the dehydration process.

Thus, in some or all embodiments of the present invention the feed components to the dehydration process are methanol, at least one promoter compound and one or both of dimethyl ether and water.

In instances where it is desired to generate the promoter in situ in the dehydration process the feed components to the process may be methanol and at least one precursor compound of a promoter compound.

Thus, in some or all embodiments of the present invention the feed components to the dehydration process are methanol, one or both of (i) at least one promoter compound and (ii) at least one precursor compound of a promoter compound; and one or both of dimethyl ether and water.

The feed components to the process may be supplied to the process in one or more feed streams.

Preferably, methyl acetate is not a component of the feed to the process.

The dehydration process is carried out as a heterogeneous process, either as a vapour phase heterogeneous process or as a liquid phase heterogeneous process.

The type of reactor used for the dehydration process is not limited, and it may be suitably carried out in any type of reactor within which a vapour phase heterogeneous process or a liquid phase heterogeneous process may be performed. Non-limiting types of reactors with which the dehydration reaction may be performed include tank reactors, multitubular reactors, plug-flow reactors, loop reactors, fluidized bed reactors, and reactive distillation columns.

The dehydration process may be carried out at a temperature of from 100 to 300° C. In some or all embodiments of the present invention, the dehydration process is carried out at a temperature of from 140 to 250° C., for example from 150 to 250° C.

Suitably, the dehydration process may be carried out at atmospheric pressure or at elevated pressure.

In some or all embodiments of the present invention, the dehydration process is carried out at a total pressure of atmospheric pressure to 3000 kPa. Where the process is conducted in the liquid phase, higher total pressures, such as 4000 kPa to 10,000 kPa, may be required to maintain the dimethyl ether product in solution.

In some or all embodiments of the present invention, the dehydration process is carried out as a heterogeneous vapour phase process at a total pressure of atmospheric pressure to 3000 kPa. In these embodiments, the temperature may be from 100 to 300° C., such as 140 to 250° C., for example from 150 to 250° C.

For vapour phase processes, the process may be carried out at a total gas hourly space velocity (GHSV) in the range 500 to 40,000 h$^{-1}$.

For liquid phase processes, the process may be carried out at a total liquid hourly space velocity (LHSV) in the range 0.2 to 20 h$^{-1}$.

The dehydration process may be carried out using one or more beds of zeolite catalyst, suitably selected from fixed bed, fluidised bed, and moving beds of catalyst.

The dehydration process may be operated as either a continuous or a batch process, preferably as a continuous process.

The dehydration process generates a crude reaction product comprising dimethyl ether and water as reaction products, unreacted methanol and one or more compounds selected from promoter compounds and promoter precursor compounds. One or more components of the crude reaction product may be recycled as feed to the process.

Dimethyl ether may be recovered from the crude reaction product by any suitable method, for example by distillation methods.

Without being bound by theory, the productivity of catalysts will typically decrease over time on stream; in industrially applied catalytic processes, one of the ways by which the decrease in productivity may be compensated for is by increasing the reaction temperature to maintain a consistent productivity. A disadvantage of increasing the temperature of the reaction is that this may lead to an increase in undesirable by-products or may result in a decrease in selectivity; another disadvantage of increasing the temperature of the reaction is that such an increase in temperature may accelerate the rate of catalyst deactivation. However, without wishing to be bound by theory, it is believed that in the present invention, decreases in productivity of the catalyst may be at least in part compensated for by increasing the relative concentration of the promoter in the methanol feed, and thus may reduce or eliminate the need for an increase in temperature to compensate for any reduction in productivity which may occur with time on stream; similarly, decreases in productivity of the catalyst may be at least in part compensated for by changing the promoter used or by adding a second or further additional promoter compound to the methanol feed as the time on stream increases.

In addition to the beneficial effect on the rate of dehydration of methanol reactions carried out in the presence of catalysts, it is believed that the use of promoters as described herein may result in an increase in the stability of the catalyst and may make the catalyst more resistant to deactivation by impurities present in the methanol feed.

In a further aspect of the present invention provides a process for dehydrating methanol to dimethyl ether product in the presence of a catalyst, wherein the catalyst is at least one aluminosilicate zeolite, and wherein prior to using the catalyst in the dehydration process, the catalyst has been impregnated with a promoter, wherein the promoter is at least one (i) aldehyde of formula $R^1CHO$ (Formula I)

wherein R1 is hydrogen, a C1-C7 C11 alkyl group or a C3-C7 C11 alkyl group in which 3 or more carbon atoms are joined to form a ring; or (ii) acetal derivative of an aldehyde of Formula I.

In this further aspect of the invention, the feed to the dehydration process comprises methanol and may optionally comprise other components, for example dimethyl ether, water, or at least one compound which is a promoter compound of Formula I or an acetal derivative of an aldehyde of Formula I.

The invention is now illustrated with reference to the following non-limiting Examples.

EXAMPLES

Details of the catalysts used in the Examples are provided in Table 1 below. In Table 1, only ring sizes of 8 T atoms or greater are provided. Smaller ring sizes have been omitted.

TABLE 1

| Catalyst | Framework Code | Framework Structure | Ring Size | SAR |
|---|---|---|---|---|
| ZSM-22 | TON | 1-D | 10 | 69 |
| PSH-3 | MWW | 2-D | 10 | 21 |
| Ferrierite | FER | 2-D | 10.8 | 20 |
| ZSM-5 | MFI | 3-D | 10 | 23 |
| Mordenite | MOR | 1-D | 12 | 20 |
| SSZ-13 | CHA | 3-D | 8 | 24 |

SAR is the silica:alumina molar ratio
1-D, 2-D and 3-D indicate a 1-dimensional, a 2-dimensional and a 3-dimensional zeolite framework structure respectively Catalysts Used in the Examples The zeolites were used in the methanol dehydration reactions of the Examples in their H-form.

All zeolites (except ZSM-22) were obtained in ammonium-form from Zeolyst International and converted to H-form by calcination in air at 500° C. The zeolite, H-ZSM-22 was prepared in accordance with the method described below.

Preparation of H-ZSM-22

For use in the preparation of the zeolite the following solutions were prepared:
i) aluminium chlorohydrol solution (25.3 g aluminium chlorohydrol in 253 g of deionised water);
ii) potassium hydroxide solution (82 g 88.8% potassium hydroxide in 820 g of deionised water);
iii) Ludox solution (900 g Ludox AS40 (silica sol with 40 wt % $SiO_2$ stabilised with ammonium hydroxide ex Aldrich) diluted in 2694 g of deionised water);
iv) ammonium chloride (200.6 g ammonium chloride in 3750 g deionised water)

The aluminium chlorohydrol solution was added slowly with vigorous stirring to the potassium hydroxide solution of to form an aluminate solution. 226 g diaminohexane (DAH) was added to the aluminate solution. The DAH/aluminate solution was added to the Ludox solution under vigorous stirring and stirred for at least 30 minutes until a gel formed. The gel was transferred to an autoclave and agitated (500 rpm) at a temperature of 160° C. for 48 hours to form a slurry. The autoclave was allowed to cool, under agitation, to a temperature below 60° C. and the slurry centrifuged to separate the solids from the mother liquor. The solids were washed with sufficient deionised water such that the pH of was less than 8 and then dried overnight at a temperature of 110° C. to generate a dried zeolitic material. The X-ray diffraction pattern of the zeolitic material showed it to be ZSM-22. The dried zeolitic material was calcined at 600° C. for 12 hours to effect removal of the diaminohexane from the pores of the pores of the zeolite. The calcined zeolite was converted into the ammonium-form of the zeolite by ion-exchange with the ammonium chloride solution at a temperature of 80° C. for 4 hours and then repeated. The ion-exchanged zeolite was separated from the liquid by filtration, washed with deionised water and dried overnight at 110° C. The ammonium-exchanged zeolite was converted to the H-form by calcination in air at 500° C. for 8 hours.

Aldehyde and Acetal Compounds Used in the Examples

The aldehydes were obtained from Sigma-Aldrich. The acetal, 1,1-dimethoxyethane was obtained from Alfa Aesar.

The methanol dehydration reactions of Examples 1 to 3 were carried out utilising the General Reaction Method and Apparatus I described below.

General Dehydration Reaction Method and Apparatus I

The methanol dehydration reactions were carried out using a 16-channel parallel fixed-bed stainless steel reactor system. Each reactor (2 mm internal diameter) was heated to maintain a temperature of 150° C. Each reactor housed a 25 mg bed of catalyst (having particle size fraction of 100 to 200 microns diameter) loaded on top of a 6 cm deep bed of an inert material (carborundum). The reactor volume above the catalyst was also packed with carborundum.

Each reactor was maintained at a temperature of 150° C. and at a total pressure of 1100 kPa throughout the reaction. A gaseous feed comprising 10 mol % methanol and inert gas was introduced into a reactor and allowed to flow through the catalyst bed for a period of 48 hours at which point a promoter compound (relative to methanol) was added to the feed to achieve a gaseous feed comprising 10 mol % methanol and 2 mol % promoter compound (relative to methanol). The gaseous feed comprising the promoter was introduced into the reactor for a period of 24 hours at a constant flow rate of methanol of 13 mmol $h^{-1}$ and a constant flow rate of promoter of 0.27 mmol $h^{-1}$.

The effluent stream from each reactor was diluted with inert gas (nitrogen) and was periodically analysed by online gas chromatography, at 3 hour intervals, to determine the yield of dimethyl ether product.

Example 1

This Example demonstrates the effect of n-butanal on the dehydration of methanol employing a variety of alumino-silicate zeolite catalysts.

With the exception of the zeolite ZSM-5, the methanol dehydration reactions were carried out using the General Reaction Method and Apparatus I described above and employing the promoter and catalysts specified in Table 2 below. In respect of ZSM-5 the reaction was carried out using the General Reaction Method and Apparatus described above but wherein methanol was fed for a period of 16 hours rather than 48 hours before the addition of 2 mol % butanal (relative to methanol) and analysed by gas chromatography at about 12 minute intervals.

The observed space time yields to dimethyl ether product are provided in Table 2.

TABLE 2

| Catalyst | Dimethyl ether STY/g $kg^{-1}$ $h^{-1}$ | |
|---|---|---|
| | No promoter | n-butanal |
| ferrierite | 2618 | 7122 |
| SSZ-13 | 1652 | 1969 |
| mordenite | 987 | 1054 |
| PSH-3 | 915 | 1265 |
| ZSM-5 | 857 | 1948 |
| ZSM-22 | 352 | 656 |

As the results in Table 2 show, the addition of t e aldehyde compound resulted in increased space time yield to dimethyl ether whereas no such increase was observed in those reactions carried out in the absence of the aldehyde.

Example 2

This Example demonstrates the effect of various iso-butanal concentrations on methanol dehydration reactions carried out in the presence of the zeolite catalysts identified in Table 3 below. Zeolite ZSM-5 was utilised in the reaction at a silica to alumina molar ratio of 80 and also at a silica to alumina molar ratio of 280. These are designated in Table 3 as ZSM-5 (80) and ZSM-5 (280) respectively.

The dehydration reactions were carried out using the General Reaction Method and Apparatus I described above utilising aldehyde concentrations relative to methanol of 2 mol % for 24 hours at an aldehyde flow rate of 0.27 mmol $h^{-1}$ followed by 5 mol % aldehyde at a flow rate of 0.67 mmol $h^{-1}$. The observed space time yields to dimethyl ether product are provided in Table 3.

TABLE 3

| Catalyst | Dimethyl ether STY/g $kg^{-1}$ $h^{-1}$ | | |
|---|---|---|---|
| | No promoter | iso-butanal 2 mol % | iso-butanal 5 mol % |
| ferrierite | 2600 | 2959 | 3354 |
| PSH-3 | 863 | 3629 | 1716 |
| ZSM-5 (80) | 395 | 1662 | 870 |
| ZSM-22 | 336 | 357 | 377 |
| ZSM-5 (280) | 94 | 489 | 394 |

As the results in Table 3 show, the use of the different concentrations of aldehyde compound provides improved productivities to dimethyl ether compared to the productivities achieved in the absence of the aldehyde compound.

Example 3

This Example demonstrates the effect of various dimethoxymethane concentrations on methanol dehydration reactions carried out in the presence of the zeolite catalysts identified in Table 4 below. Zeolite ZSM-5 was utilised in the reaction at a silica to alumina molar ratio of 23 and also at silica to alumina molar ratios of 80 and 280. These are designated in Table 4 as ZSM-5 (23), ZSM-5 (80) and ZSM-5 (280), respectively.

The dehydration reactions were carried out using the General Reaction Method and Apparatus I described above utilising aldehyde concentrations relative to methanol of 2 mol % for 24 hours at a dimethoxymethane flow rate of 0.27 mmol $h^{-1}$ followed by 10 mol % aldehyde at a flow rate of 1.3 mmol h$^{-1}$. The observed space time yields to dimethyl ether product are provided in Table 4.

TABLE 4

| Catalyst | Dimethyl ether STY/g kg$^{-1}$ h$^{-1}$ | | |
|---|---|---|---|
| | No promoter | dimethoxymethane 2 mol % | dimethoxymethane 10 mol % |
| SSZ-13 | 1352 | 1454 | 1663 |
| ZSM-5 (23) | 846 | 867 | 903 |
| ZSM-5 (80) | 380 | 398 | 444 |
| ZSM-22 | 341 | 364 | 430 |
| ZSM-5 (280) | 84 | 86 | 100 |

As the results in Table 4 show, the use of the different concentrations of dimethoxymethane provides improved productivities to dimethyl ether compared to the productivities achieved in the absence of the dimethoxymethane.

Examples 4 and 5

The methanol dehydration reactions of Examples 4 and 5 were carried out utilising the General Reaction Method and Apparatus II described below.

General Reaction Method and Apparatus II

The methanol dehydration reactions were carried out using a 16-channel parallel fixed-bed stainless steel reactor system. Each reactor (10 mm internal diameter) housed a bed of catalyst mixed with silica dioxide diluent (0.337 g catalyst diluted with 1.348 g silica dioxide). The catalyst and silica dioxide each had a particle size of 450 to 900 microns diameter. The mixture was loaded on top of a 6.5 cm deep bed of an inert material (quartz sand). The reactor volume above the catalyst was also packed with quartz sand.

Each reactor was maintained at a temperature of 160° C., and at a total pressure of 1100 kPa throughout the reactions. A gaseous feed comprising 10 mol % methanol and inert gas was introduced into the reactor and allowed to flow through the catalyst bed for a period of 100 hours at which point a promoter compound was added to the feed to achieve a gaseous feed comprising 10 mol % methanol and 0.23 mol % promoter compound (relative to methanol). This gaseous feed comprising the promoter compound was fed to the reactor for a period of 120 hours at a constant methanol flow rate of 90 mmol h$^{-1}$ and a constant promoter flow rate of 0.2 mmol h$^{-1}$.

The effluent stream from each reactor was cooled down to 5° C. in a condenser. The gas phase effluent stream from the condenser was periodically analysed by online gas chromatography to determine the yield of dimethyl ether product.

Example 4

In this Example, the effect of the acetal 1,1-dimethoxyethane was investigated in methanol dehydration reactions employing the zeolites, mordenite and ferrierite.

The methanol dehydration reactions were carried out using the General Reaction Method and Apparatus II described above and wherein the concentration of aldehyde relative to methanol was 0.23 mol %.

The observed space time yields to dimethyl ether product are also provided in Table 5 below.

TABLE 5

| Catalyst | DME STY/g kg$^{-1}$ h$^{-1}$ | |
|---|---|---|
| | No promoter | 1,1-dimethoxyethane |
| ferrierite | 1014 | 1305 |
| mordenite | 915 | 1019 |

As can be seen from Table 5, the space time yields to dimethyl ether were higher in the reactions carried out with the addition of the acetal compound compared to the reactions carried out in the absence of the acetal.

Example 5

This Example demonstrates the effect of various n-octanal concentrations on methanol dehydration reactions.

The dehydration reactions were carried out using the General Reaction Method and Apparatus II described above using the zeolite ZSM-22 as catalyst except the gaseous feed comprising 10 mol % methanol and inert gas initially introduced into the reactors was supplied for a period of 170 hours, instead of 100 hours, and wherein at 170 hours, n-octanal was added to the feed to achieve a gaseous feed comprising 10 mol % methanol and 0.5 mol % n-octanal relative to methanol. This feed was supplied to the reactors for a period of 169 hours whereupon the addition of n-octanal was ceased and a gaseous feed comprising 10 mol % methanol continued to be introduced into the reactors for a period of 43 hours. At 382 hours on stream n-octanal was added to the gaseous feed such that the feed comprised 10 mol % methanol and an n-octanal concentration of 2 mol % relative to methanol. This gaseous feed was supplied to the reactors for a period of 47 hours whereupon the addition of n-octanal was ceased and the reactions were allowed to continue for a further period of 61 hours with a gaseous feed comprising 10 mol % methanol and inert gas. The results of this Example are shown in FIG. 1. As is illustrated in FIG. 1, during the periods in which the aldehyde promoter was a component of the feed, the space time yields (STY) to dimethyl ether was observed to increase. In the periods where the aldehyde was not employed in the feed, the STY to dimethyl ether was seen to decrease. It was also observed that the STY's to dimethyl ether achieved in the periods which followed the addition of aldehyde compound (i.e. 339 to 382 hours on stream and 439 to 500 hours on stream), were higher than the dimethyl ether STY seen in initial methanol only period (0 to 179 hours on stream).

Example 6

In this Example, the effect of the straight chain n-butanal and the branched chain iso-butanal was investigated in methanol dehydration reactions employing the zeolite ferrierite.

The methanol dehydration reactions were carried out using the General Reaction Method and Apparatus I described above and employing the aldehyde promoters at a concentration of 2 mol % relative to methanol.

Figure 2:
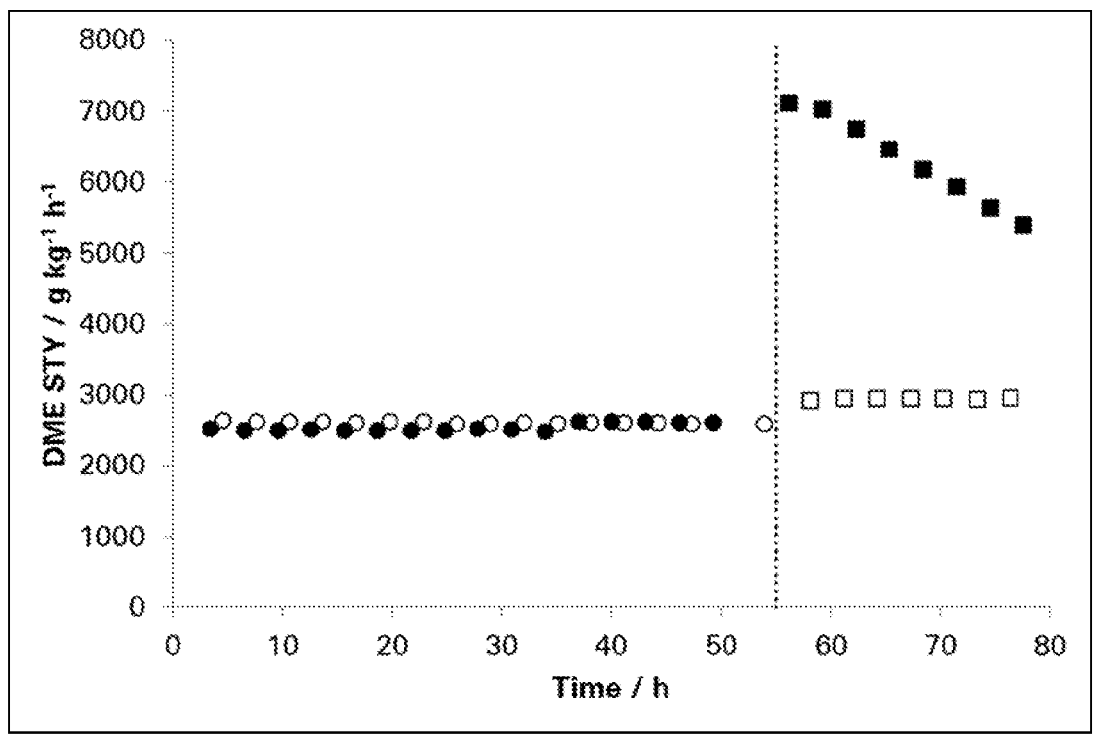
FIG. 2 depicts STY to dimethyl ether in the dehydration of methanol in the presence of the zeolite ferrierite as catalyst and in the presence of straight and branched chain $C_4$ aldehydes.

The results of this Example are shown in FIG. 2. In FIG. 2, the circles represent periods in which methanol was used as the feed to the process i.e. no aldehyde addition; the black squares represent periods in which 2 mol % of n-butanal (relative to methanol) was present in the methanol feed and the white squares represent periods in which 2 mol % of iso-butanal (relative to methanol) was present in the methanol feed. As is illustrated in FIG. 2, during the periods in which an aldehyde promoter was used, the space time yield (STY) to dimethyl ether was observed to increase compared to the periods carried out in the absence of the aldehyde promoter. It was also observed that the use of the branched chain aldehyde, iso-butanal, resulted in little or no catalyst deactivation.

The invention claimed is:

1. A process comprising dehydrating methanol to dimethyl ether product in the presence of a catalyst and a promoter, wherein the catalyst is at least one aluminosilicate zeolite and the promoter is at least one
   (i) aldehyde of formula $R^1CHO$ (Formula I)
      wherein $R^1$ is a $C_3$-$C_{11}$ alkyl group or a $C_3$-$C_{11}$ alkyl group in which 3 or more carbon atoms are joined to form a ring; or
   (ii) acetal derivative of an aldehyde of Formula I; and
wherein the molar ratio of promoter to methanol is maintained at 0.1 or less.

2. A process according to claim 1 wherein $R^1$ is a $C_3$-$C_7$ alkyl group.

3. A process according to claim 1 wherein $R^1$ is a straight or branched alkyl chain group.

4. A process according to claim 3 wherein $R^1$ is a straight alkyl chain group and the aldehyde of Formula I is selected from the group consisting of n-butanal, n-hexanal and n-octanal.

5. A process according to claim 3 wherein $R^1$ is a branched alkyl chain group and the aldehyde of Formula I is selected from the group consisting of iso-butanal and 2-ethyl hexanal.

6. A process according to claim 1 wherein the acetal derivative of the aldehyde of Formula I is a dimethoxyacetal.

7. A process according to claim 1 wherein the total amount of promoter relative to the total amount of methanol is maintained in an amount of 0.0001 to 10 mol %.

8. A process according to claim 1 wherein the molar ratio of promoter to methanol is maintained in the range 0.00001:1 to 0.1:1.

9. A process according to claim 1 wherein the promoter is generated in-situ in the process.

10. A process according to claim 1 wherein the zeolite is selected from the group consisting of zeolites of framework type FER, MWW, MTT, MFI, MOR, FAU, CHA, BEA and TON.

11. A process according to claim 1 wherein the zeolite is a large pore zeolite and $R^1$ is a straight or branched chain $C_3$-$C_7$ alkyl group.

12. A process according to claim 1 wherein the zeolite is a medium pore zeolite and $R^1$ is a straight chain $C_3$-$C_7$ alkyl group.

13. A process according to claim 1 wherein the zeolite is a 2-dimensional medium pore zeolite and $R^1$ is a branched chain $C_3$ alkyl group.

14. A process according to claim 1 wherein the acetal derivative of the aldehyde of Formula I is a dimethoxyacetal and the zeolite is a zeolite of framework type selected from the group consisting of TON, MOR and FER.

15. A process according to claim 1 wherein the zeolite is a hydrogen-form zeolite.

16. A process according to claim 1 wherein the zeolite is composited with a binder material.

17. A process according to claim 1 wherein the process is carried out at a temperature of from 100° C. to 300° C.

18. A process according to claim 1 wherein the process is carried out as a heterogeneous vapour phase process.

19. The process of claim 1, wherein the promoter improves the productivity to dimethyl ether product.

20. A process comprising dehydrating methanol to dimethyl ether in the presence of a catalyst and a promoter, and in the absence of methyl acetate, wherein the catalyst is at least one aluminosilicate zeolite and the promoter is at least one
   (i) aldehyde of formula $R^1CHO$ (Formula I)
      wherein $R^1$ is hydrogen, a $C_1$-$C_{11}$ alkyl group or a $C_3$-$C_{11}$ alkyl group in which 3 or more carbon atoms are joined to form a ring; or
   (ii) acetal derivative of an aldehyde of Formula I; and
wherein the molar ratio of promoter to methanol is maintained at 0.1 or less.

21. A process according to claim 20 wherein the molar ratio of promoter to methanol is maintained in the range 0.00001:1 to 0.1:1.

* * * * *